United States Patent
Pillai et al.

(10) Patent No.: US 6,565,864 B2
(45) Date of Patent: May 20, 2003

(54) SKIN CARE PRODUCT CONTAINING RETINOIDS AND PHYTOESTROGENS IN A DUAL COMPARTMENT PACKAGE

(75) Inventors: Sreekumar Pillai, Wayne, NJ (US); Stewart Paton Granger, Paramus, NJ (US); Ian Richard Scott, Allendale, NJ (US); David Joseph Pocalyko, Wayne, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/036,589

(22) Filed: Nov. 7, 2001

(65) Prior Publication Data

US 2002/0127255 A1 Sep. 12, 2002

Related U.S. Application Data

(60) Provisional application No. 60/258,456, filed on Dec. 28, 2000.

(51) Int. Cl.[7] ............ A61K 7/00; A61K 31/35; A61K 31/19
(52) U.S. Cl. .......... 424/401; 514/456; 514/570
(58) Field of Search ............ 424/401; 514/456, 514/570

(56) References Cited

U.S. PATENT DOCUMENTS

| 5,728,726 A | | 3/1998 | Giese et al. |
| 5,788,972 A | * | 8/1998 | De Salvert et al. |
| 5,834,513 A | * | 11/1998 | Ptchelintsev et al. |
| 5,847,003 A | | 12/1998 | Ptchelintsev et al. |
| 5,914,116 A | * | 6/1999 | Suares et al. |

FOREIGN PATENT DOCUMENTS

| EP | 0745375 A1 | * | 4/1996 |
| EP | 1000613 A2 | * | 5/2000 |
| WO | 93/19743 | | 10/1993 |
| WO | WO 96/37420 | * | 11/1996 |
| WO | WO 01/08650 A1 | * | 2/2001 |
| WO | WO 01/30314 A1 | * | 5/2001 |
| WO | WO 01/35920 A1 | * | 5/2001 |

OTHER PUBLICATIONS

"Isotretinoin Treatment of Severe Acne Affects the Endogenous Concentration of Vitamin A in Sebaceous Glands," A. Vahlquist et al., Journal of Invest. Dermatology, vol. 94, (1990), pp. 496–498.

"Treatment of Actinically Aged Skin with Topical Tretinoin", C.N. Ellis et al., Vasel, Karger, vol. 3 (1989(, pp. 249–252.

"Effect of a Conjugated Oestrogen Cream (Premarin®) on Aging Facial Skin," Maturitas 19, p. 211–213, (1994).

PCT International Search Report for International appln. No. PCT/EP/14483 dated Jul. 11, 2002.*

* cited by examiner

Primary Examiner—Theodore J. Criares
Assistant Examiner—Jennifer Kim
(74) Attorney, Agent, or Firm—Ellen Plotkin

(57) ABSTRACT

A stable skin care product containing a first composition comprising about 0.001% to about 10% of a retinoid; a second composition comprising about 0.001% to about 10% of a phytoestrogen; a first compartment for storing the first composition; and a second compartment for storing the second composition, the first and second compartments being joined together.

5 Claims, No Drawings

SKIN CARE PRODUCT CONTAINING RETINOIDS AND PHYTOESTROGENS IN A DUAL COMPARTMENT PACKAGE

This application claims priority of provisional application Serial No. 60/258,456, filed Dec. 28, 2000.

FIELD OF THE INVENTION

The invention relates to stable skin care compositions containing a retinoid in a first compartment and a phytoestrogen in a second compartment of a dual compartment package.

BACKGROUND OF THE INVENTION

Retinoids (e.g. retinol and retinyl esters) are common ingredients used in cosmetic products. Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g. Vahlquist, A. et al., *J. Invest. Dermatol.*, Vol. 94, Holland D. B. and Cunliffe, W. J. (1990), pp. 496–498; Ellis, C. N. et. Al., "Pharmacology of Retinols in Skin," *Basel, Karger,* Vol. 3, (1989), pp. 249–252; and PCT Patent Application No. WO 93/19743.

Retinoid metabolism, however may result in conversion of the retinoid to non-beneficial by-products, thus yielding a lesser amount of beneficial retinoic acid to treat skin conditions. Several references, therefore, teach the use of a variety of natural actives for aiding in the treatment of skin conditions such as acne, wrinkles, psoriasis, age spots, and discoloration. For example, phytoestrogens (i.e., natural compounds which have estrogen-like activity and which are found in plants) have been increasingly used for cosmetic and therapeutic purposes. Estrogens and synthetic compounds which act like estrogens are known to increase the thickness of the dermal layer and reduce the wrinkle formation in the aging skin. Changes in the skin such as skin dryness, loss of skin elasticity and plumpness occurring after menopause are attributed to the lack of estrogen production. Estrogen therapy prevents or slows down many of the changes associated with aging skin (Creidi et al., "Effect of a Conjugated Oestrogen Cream (Premarin®) on Aging Facial Skin," *Maturitas,* 19, p. 211–213, 1994).

Several phytoestrogens have been disclosed for cosmetic benefits. For example, U.S. Pat. No. 5,728,726 teaches the use of genistein for thyrosine kinase inhibitory activity. U.S. Pat. Nos. 5,847,003 and 5,834,513, assigned to Avon, disclose the use of oxacids and oxadiacids in combination with retinoids. Both Avon patents disclose the use of antioxidant bioflavonoids, such as genistein and daidzein, as optional ingredients.

It has been discovered, however, that phytoestrogens induce oxidation of retinol, and therefore contribute to retinol degradation. Although multi-compartment systems for delivering compositions have been described, the need to separate phytoestrogens from retinoids has not been disclosed. For example, U.S. Pat. No. 5,914,116, issued to the assignee of the present invention, describes two separate containers for separating two different skin actives to provide dual skin benefits with one compartment containing retinoids and the second compartment containing a second active providing a second and different benefit.

Therefore, there still exists a need for compositions that provide the skin benefits of retinoids with the retinoid enhancing benefits of phytoestrogens.

SUMMARY OF THE INVENTION

A stable skin care product containing:
   a first composition comprising about 0.001% to about 10% of a retinoid;
   a second composition comprising about 0.001% to about 10% of a phytoestrogen;
   a first compartment for storing the first composition; and
   a second compartment for storing the second composition, the first and second compartments being joined together.

DETAILED DESCRIPTION

As used herein, the term "comprising" means including, made up of, composed of, consisting and/or consisting essentially of. Except in the operating and comparative examples, or where otherwise explicitly indicated, all numbers in this description indicating amounts or ratios of materials or conditions of reaction, physical properties of materials and/or use are to be understood as modified by the word "about".

The term "conditioning" as used herein means prevention and treatment of dry skin, acne, photodamaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation.

The inventive compositions contain, as a preferred ingredient, a retinoid, which is selected from retinyl esters, retinol, retinal and retinoic acid, preferably retinol or retinyl ester. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecanoate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest. Retinyl linoleate and retinyl oleate are also preferred due to their efficacy.

Retinol or retinyl ester is employed in the inventive composition in an amount of about 0.001% to about 10%, preferably in an amount of about 0.01% to about 1%, most preferably in an amount of about 0.01% to about 0.5%.

Phytoestrogens

As part of the present invention, it has been surprisingly found that phytoestrogens synergistically improve the skin benefits of retinoids. Essentially, phytoestrogens increase the sensitivity of the skin to retinoids.

Therefore, the present invention contains about 0.001% to about 10% of at least one phytoestrogen in the second composition.

Phytoestrogens include flavonoids such as estrogenic flavonoids, genistein, daidzein, glycitin, biochanin A, formononetin and equol and mixtures thereof, acetyl and malonyl esters of genistein and daidzein, and glucosides of genistein and daidzein. It should be noted that the aforementioned list is not exclusive, and may include other phytoestrogens known to persons of ordinary skill in the art.

Dual Compartment Package

Compositions which include retinoids are generally unstable and may undergo chemical degradation. As a further retinoid enhancing benefit, phytoestrogens are an essential component of the present invention. Phytoestrogens such as genistein and daidzein synergistically interact with retinoids to deliver skin benefits. However, phytoestrogens contribute to the oxidation, and thus the degradation of retinoids. The phytoestrogen induced retinol destabilization dramatically reduces the overall efficacy of the boosted retinoid composition when both ingredients are contained in a single formula. Therefore, in order to protect against retinoid breakdown while still providing the synergistically beneficial effects of phytoestrogens, the present invention provides a dual compartment package that contains a first composition containing retinoids in a first compartment and a second composition containing at least one phytoestrogen in a second compartment. The first composition provides a first benefit to the skin while the second composition works to boost or enhance the effect of the first benefit.

The dual compartment package may be designed in various ways known to persons of ordinary skill in the art as long as the purpose of providing the first and second compositions in two separate containers is achieved. In one embodiment, the dual compartment package is in the form of two jars or bottles adjoiningly attached. In a second embodiment, the dual compartment package is in the form of a single bottle/jar with a division separating an interior of the bottle/jar into a first and second compartment. Other embodiments are contemplated as being within the scope of the present invention as long as the compositions are retained separately.

Cosmetically Acceptable Vehicle

The product according to the present invention also comprises a cosmetically acceptable vehicle to act as a dilutant, dispersant, or carrier for the active components in the either or both the first and second compositions, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

Optional Skin Benefit Materials and Cosmetic Adjuncts

In either one or both of the first and second compositions of the present invention, an oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in either one or both of the first and second cosmetic compositions of the present invention and are described below. Actives are defined as skin or hair benefit agents other than emollients and other than ingredients that merely improve the physical characteristics of the composition. Although not limited to this category, general examples include sunscreens, skin lightening agents, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9, 13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into one or both of the first and second cosmetic compositions of the cosmetic product of the present invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into one or both of the first and second compositions of the cosmetic product of the present invention. These ingredients may include coloring agents, opacifiers and perfumes. Amounts of these materials may range anywhere from 0.001% up to 20% by weight of the composition.

The first and second compositions of the cosmetic product of the present invention are intended primarily as a product for topical application to human skin, especially as an agent for conditioning and smoothening the skin, and preventing or reducing the appearance of wrinkled or aged skin.

In use, a small quantity of the first composition, for example from 1 to 5 ml, is applied to exposed areas of the skin, from a suitable container or applicator and, if necessary, it is then spread over and/or rubbed into the skin using the hand or fingers or a suitable device. Simultaneously, a small quantity of the second composition, for example from 1 to 5 ml, is applied to exposed areas of the skin, from a suitable container or applicator and, if necessary, it is also spread over and/or rubbed into the skin using the hand or fingers or a suitable device. Therefore, depending upon the intensity of treatment benefits desired, the first and second compositions may be used alone, simultaneously, or in consecutive order.

Product Form and Packaging

The topical skin treatment composition of the invention can be formulated as a lotion, a fluid cream, a cream or a gel.

EXAMPLE 1

Synergy of Retinoids and Phytoestrogens
(a) Cell Culture Method

Human adult fibroblasts obtained from sun-protected inner arm of 25–30 year female volunteer were used in this. Cells were grown in 1:1 DMEM/Hams F12 media containing 10% FBS, maintained at 37° C. in a 5% $CO_2$ atmosphere under normal atmosphere oxygen tension. Third passage adult fibroblasts were grown in DMEM media with 10% FBS in 12-well plates at a seeding density of 2500 cells/ml/well. The cells at 80% confluence were rinsed in serum free and phenol red free (PRF) DMEM media twice. Pretreatment with phyto-compounds for 4 hours was conducted and then dosed with retinoids and was incubated for 48 hours. After the incubation, the wells were washed twice with 1×PBS and the cell monolayer was harvested in 100 $\mu$l cell lysis buffer (contains 1×PBS, 1% Triton X, 0.5% sodium deoxycholate, 0.1% SDS containing protease inhibitor (10 mg/ml PMSF in isopropanol, 10 $\mu$l/ml). The suspension was spun at 14000 rpm for 10 minutes, the supernatant collected and an aliquot of this supernatant was used for protein quantification. Protein concentration was determined using Pierce protein kit. The remainder of 100 $\mu$l supernatant (cell lysate) was denatured in a mixture of 40 $\mu$l sample buffer (NOVEX) and 0.5% Beta mercaptoethanol (BME) and by boiling the sample for 5 minutes. Equal amount of protein was then loaded onto 16% Tris-glycine gels for protein analysis by SDS page and Western Immuno-blotting for CRABP-2 protein expression.

(b) Detection of Cellular Retinoic Acid Binding Protein 2 (CRABP-2)

Within the cells, retinol and retinoic acid are bound to specific cellular binding proteins, 2 of the major proteins are CRABP-1 and 2 (Roos et al., *Pharmacological Reviews* 50: 315–333, 1998). These proteins act in regulating the intracellular concentration of retinoids by acting as both storage or shuttle proteins in retinoid metabolism. High or low levels of retinoids cause cell damage, including cell death, therefore regulation of constant levels of retinoids and its binding proteins are very critical for cell survival. The levels of this protein are regulated by the amount of retinoic acid within the cells. Higher cellular levels of retinoids increase the expression of CRABP-2. Therefore, the amount of this protein in the cells, is a measure of the retinoid activity of the cells. Skin cells contain high levels of CRABP-2 both in the epidermis and the dermis. CRABP-2 response to retinoid administration in fibroblasts in vitro is used as a reproducible measure of retinoid bioactivity that predict human skin responses. (Elder et al., *J. Invest. Dermatol.*, 106: 517–521, 1996). Increase in CRABP-2 is also associated with increased epidermal differentiation, and dermal retinoid action. Therefore, in these studies CRABP-2 expression of fibroblasts was used as a measure of retinoid activity leading to increased epidermal differentiation (skin conditioning and dry skin benefit) and dermal collagen and extracellular matrix synthesis (anti-aging, anti-wrinkling benefits).

To measure the levels of CRABP-2 in the fibroblasts, the equal amount of protein of cell supernatant were loaded onto nitrocellulose blots in a dot blot apparatus as instructed by the manufacturer, and immunostaining was carried out using monoclonal antibodies to CRABP-2 according to standard procedures. The CRABP-2 protein band was visualized in the Dot Blots using the chemiluminescence system obtained from Santa Cruz Biotechnology (SantaCruz, Calif.). The bands in the film were quantitated by dens tometric scanning, the data from the triplicate samples were calculated as % of control and expressed in the following tables as % increase over control (with control as 100%) +/–SD triplicates.

EXAMPLE 2
Stability of Retinol in the Presence of Phytoestrogenic Flavonoids

Retinol was dissolved as a 10% solution in aqueous ethanol (1:1 water:ethanol). This solution was diluted to 0.001%, or approximately 30 $\mu$M). This solution gave an OD of about 0.35 absorption unit at 360 nm in a 96 well plate spectrophotometer.

Aqueous ethanolic stock solutions of the genistein, daidzein were prepared as 0.1%, 0.01% or 0.001%. To 200 $\mu$l of 0.001% retinol solution in a 96 well plate was added 20 $\mu$l of the flavonoid (i.e. 1–10 dilution) giving a final flavonoid concentration of 0.01, 0.001 and 0.0001%. The plates were mixed and an initial OD reading was taken at 360 nm. The plates were incubated at room temperature in the dark for up to 2 days and subsequent readings were taken at 8, 24 and 48 hours. The OD readings at these time points were normalized to the 0 time point reading. The retinol stability was expressed as % of retinol (OD reading) at 0 time. The data is shown in the tables below.

In the 2 tables shown below, synergy between genistein and daidzein and retinoids were tested. In both the studies genistein was delivered to the cells in a soluble form in DMSO: ethanol. 1 $\mu$M genistein alone stimulated CRABP-2 significantly. Both genistein and daidzein stimulate retinoid activity in a synergistic manner. All the retinoids tested, except retinyl acetate showed synergy with genistein and daidzein. These data support the claim that the phytoestrogenic flavonoids genistein and daidzein, when supplied to cells in a soluble form, synergistically enhanced the activity of retinoids.

TABLE 1

Synergy between genistein and retinoids

| | CRABP-2 production | % as Control | P value vs. Control $p < 0.05$ | P value vs. retinoids $p < 0.05$ | Synergy |
|---|---|---|---|---|---|
| Control | 0.29 +/– 0.07 | 100 +/– 27 | 1 | | |
| 10 nM Retinoic acid | 1.24 +/– 0.29 | 428 +/– 101 | 0.0055 | 1 | |
| 1 nM Retinoic acid | 0.97 +/– 0.47 | 335 +/– 162 | 0.068 | 1 | |
| 100 nM Retinyl Linoleate | 0.52 +/– 0.3 | 181 +/– 110 | 0.28 | 1 | |
| 100 nM Retinyl Palmitate | 1.26 +/– 0.51 | 434 +/– 177 | 0.032 | 1 | |
| 100 NM Retinyl Acetate | 0.60 +/– 0.32 | 209 +/– 118 | 0.19 | 1 | |
| 1 $\mu$M Genistein | 1.9 +/– 0.71 | 655 +/– 247 | 0.018 | | |
| 1 $\mu$M Genistein + 10 nM Retinoic acid | 4.18 +/– 031 | 1441 +/– 108 | 3.23E–05 | 2.96E–04 | YES |
| 1 $\mu$M Genistein + 1 nM Retinoic acid | 4.01 +/– 0.61 | 1383 +/– 394 | 0.00049 | 0.012 | YES |
| 1 $\mu$M Genistein + 100 nM Retinyl linoleate | 4.08 +/– 1.14 | 1408 +/– 213 | 0.0045 | 0.000982 | YES |
| 1 $\mu$M Genistein + 100 nM Retinyl palmitate | 4.32 +/– 0.13 | 1489 +/– 47 | 160E–06 | 5.76E–04 | YES |
| 1 $\mu$M Genistein + 100 nM Retinyl acetate | 2.32 +/– 0.91 | 800 +/– 313 | 1.80E–02 | 3.80E–02 | NO |

TABLE 2

Synergy Between Daidzein and Retinoids

| | CRABP-2 production | % as Control | P value vs. Control $p < 0.05$ | P value vs. retinoids $p < 0.05$ | Synergy |
|---|---|---|---|---|---|
| Control | 0.29 +/– 0.07 | 100 +/– 27 | 1 | | |
| 10 nM Retinoic acid | 1.24 +/– 0.29 | 428 +/– 101 | 0.0055 | 1 | |
| 1 nM Retinoic acid | 0.97 +/– 0.47 | 335 +/– 162 | 0.068 | 1 | |
| 100 nM Retinyl Linoleate | 0.52 +/– 0.3 | 181 +/– 110 | 0.28 | 1 | |
| 100 nM Retinyl Palmitate | 1.26 +/– 0.51 | 434 +/– 177 | 0.032 | 1 | |

TABLE 2-continued

Synergy Between Daidzein and Retinoids

| | CRABP-2 production | % as Control | P value vs. Control p < 0.05 | P value vs. retinoids p < 0.05 | Synergy |
|---|---|---|---|---|---|
| 100 NM Retinyl Acetate | 0.60 +/− 0.32 | 209 +/− 118 | 0.19 | 1 | |
| 1 μM Daidzein | 1.49 +/− 0.66 | 513 +/− 227 | 0.035 | | |
| 1 μM Daidzein + 10 nM Retinoic acid | 3.42 +/− 1.01 | 1181 +/− 350 | 0.0059 | 0.023 | YES |
| 1 μM Daidzein + 1 nM Retinoic acid | 3.52 +/− 0.47 | 1213 +/− 163 | 0.000309 | 0.027 | YES |
| 1 μM Daidzein + 100 nM Retinyl linoleate | 3.29 +/− 0.14 | 1136 +/− 142 | 0.00024 | 0.00078 | YES |
| 1 μM Daidzein + 100 nM Retinyl palmitate | 2.51 +/− 0.19 | 865 +/− 65 | 4.90E−05 | 1.69E−02 | YES |
| 1 μM Daidzein + 100 nM Retinyl acetate | 2.27 +/− 1.4 | 782 +/− 489 | 0.07 | 0.11 | NO |

EXAMPLE 3

The following tables show the effect of genistein and daidzein on destabilizing retinol. The experiment was done as described in methods section. The OD readings from duplicate measurements were averaged and given here.

TABLE 3

Retinol stability in the presence of Genistein:

| Time(hours) | 0% Genistein | 0.0001% | 0.01% | 0.01% |
|---|---|---|---|---|
| 8 | 92 | 84 | 82 | 82 |
| 24 | 86 | 76 | 74 | 80 |
| 48 | 81 | 77 | 73 | 76 |

TABLE 4

Retinol stability in the presence of Daidzein

| Time (hours) | 0% Daidzein | 0.0001% | 0.001% | 0.01% |
|---|---|---|---|---|
| 8 | 92 | 82 | 80 | 73 |
| 24 | 86 | 78 | 79 | 69 |
| 48 | 81 | 76 | 76 | 68 |

Retinol alone in the absence of any agents degraded slowly (8% by 8 hours, 14% by 24 hours and 19% by 48 hours). However, in the presence of genistein and daidzein the degradation of retinol was accelerated. As early as 8 hours, 16–18% of retinol was degraded in the presence of these flavonoids. This suggests that both genistein and daidzein caused marked increases in the instability of retinol. This will make it necessary to use special packaging, one compartment for retinol and another for the flavonoids in products containing retinoids and the flavonoids.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the inventions be limited only by the scope of the claims which follow, and that such claims be interpreted as broadly as is reasonable. Throughout this application, various publications have been cited. The entireties of each of these publications are hereby incorporated by reference herein.

What is claimed is:

1. A stable skin care product containing:

a first composition comprising from about 0.01% to about 1% of a retinoid to provide a first benefit;

said retinoid selected from a group consisting of retinyl esters, retinol, retinal, and mixtures thereof;

a second composition comprising about 0.001% to about 10% of at least one phytoestrogen, the phytoestrogen boosting the first benefit; said phytoestrogen selected from the group consisting of genistein, daidzein, glycitein, biochanin A, formononetin, equol, and mixtures thereof;

a first compartment for storing the first composition; and a second compartment for storing the second composition, the first and second compartments being joined together;

wherein said first and said second compositions are provided in synergistic effective amounts.

2. The stable skin care product of claim 1 wherein the second composition has at least two phytoestrogens in an amount of about 0.001% to about 10%.

3. A method of conditioning skin, the method comprising applying topically to the skin the product of claim 1.

4. A method of mimicking the effect on skin of retinoic acid, the method comprising applying to the skin the product of claim 1.

5. The stable skin care product of claim 1, wherein said phytoestrogen is selected from the group consisting of genistein, daidzein, and mixtures thereof.

* * * * *